US011439309B2

(12) United States Patent
Dharmakumar et al.

(10) Patent No.: US 11,439,309 B2
(45) Date of Patent: *Sep. 13, 2022

(54) ASSESSMENT OF CORONARY HEART DISEASE WITH CARBON DIOXIDE

(75) Inventors: Rohan Dharmakumar, Moorpark, CA (US); Debiao Li, San Marino, CA (US); Sotirios A. Tsaftaris, Lucca (IT)

(73) Assignee: Cedars-Sinai Medical Center, Los Angeles, CA (US)

( * ) Notice: Subject to any disclaimer, the term of this patent is extended or adjusted under 35 U.S.C. 154(b) by 305 days.

This patent is subject to a terminal disclaimer.

(21) Appl. No.: 14/115,860

(22) PCT Filed: May 7, 2012

(86) PCT No.: PCT/US2012/036813
§ 371 (c)(1),
(2), (4) Date: Nov. 5, 2013

(87) PCT Pub. No.: WO2012/151583
PCT Pub. Date: Nov. 8, 2012

(65) Prior Publication Data
US 2014/0088406 A1  Mar. 27, 2014

Related U.S. Application Data

(60) Provisional application No. 61/482,956, filed on May 5, 2011.

(51) Int. Cl.
*A61B 5/02* (2006.01)
*A61B 5/055* (2006.01)
(Continued)

(52) U.S. Cl.
CPC ........ *A61B 5/02007* (2013.01); *A61B 5/0035* (2013.01); *A61B 5/026* (2013.01);
(Continued)

(58) Field of Classification Search
None
See application file for complete search history.

(56) References Cited

U.S. PATENT DOCUMENTS 5,558,083 A    9/1996  Bathe et al.
5,670,177 A    9/1997  Briend et al.
(Continued)

FOREIGN PATENT DOCUMENTS

AU    2012250539 A1    12/2013
CA    2845308 A1    11/2012
(Continued)

OTHER PUBLICATIONS

Wacker et al., "Changes in Myocardial Oxygenation and Perfusion Under Pharmacological Stress With Dipyridamole: Assessment Using T*2 and T1 Measurements," Magnetic Resonance in Medicine, 41:686-695 (1999).*

(Continued)

*Primary Examiner* — James M Kish
(74) *Attorney, Agent, or Firm* — Nixon Peabody LLP; Linda B. Huber; Suwei Zhu

(57) ABSTRACT

The invention provides methods for diagnosing coronary heart disease in a subject in need thereof comprising administering an admixture comprising $CO_2$ to a subject to reach a predetermined $PaCO_2$ in the subject to induce hyperemia, monitoring vascular reactivity in the subject and diagnosing the presence or absence of coronary heart disease in the subject, wherein decreased vascular reactivity in the subject compared to a control subject is indicative of coronary heart disease. The invention also provides methods for increasing sensitivity and specificity of BOLD MRI.

21 Claims, 12 Drawing Sheets

(51) Int. Cl.

| | | |
|---|---|---|
| *A61B 8/08* | (2006.01) | |
| *A61B 5/145* | (2006.01) | |
| *A61B 5/318* | (2021.01) | |
| *A61B 5/00* | (2006.01) | |
| *A61B 5/026* | (2006.01) | |
| *A61B 6/03* | (2006.01) | |
| *A61B 6/00* | (2006.01) | |
| *A61B 7/02* | (2006.01) | |
| *A61B 8/00* | (2006.01) | |
| *A61D 7/00* | (2006.01) | |
| *A61M 16/12* | (2006.01) | |
| *G01R 33/48* | (2006.01) | |
| *G01R 33/60* | (2006.01) | |

(52) U.S. Cl.
CPC .......... *A61B 5/02028* (2013.01); *A61B 5/055* (2013.01); *A61B 5/145* (2013.01); *A61B 5/318* (2021.01); *A61B 6/032* (2013.01); *A61B 6/4417* (2013.01); *A61B 7/02* (2013.01); *A61B 8/0883* (2013.01); *A61B 8/4416* (2013.01); *A61B 8/488* (2013.01); *A61D 7/00* (2013.01); *A61M 16/12* (2013.01); *G01R 33/481* (2013.01); *G01R 33/4806* (2013.01); *G01R 33/4812* (2013.01); *G01R 33/4814* (2013.01); *G01R 33/60* (2013.01); *A61B 5/7257* (2013.01); *A61B 6/037* (2013.01); *A61B 6/507* (2013.01); *A61B 6/508* (2013.01)

(56) References Cited

U.S. PATENT DOCUMENTS

| | | | |
|---|---|---|---|
| 5,975,748 | A | 11/1999 | East, IV et al. |
| 6,001,332 | A | 12/1999 | Garrett |
| 6,013,243 | A | 1/2000 | Achilefu |
| 7,073,501 | B2 | 7/2006 | Remmers et al. |
| 7,941,204 | B1* | 5/2011 | Wang ............. A61B 5/055 600/410 |
| 8,290,226 | B2* | 10/2012 | Guhring ........... A61B 5/055 600/427 |
| 8,936,777 | B2* | 1/2015 | Cesati ............ A61K 51/0459 424/1.89 |
| 2002/0103454 | A1 | 8/2002 | Sackner et al. |
| 2002/0185129 | A1* | 12/2002 | Fisher et al. ............. 128/203.25 |
| 2003/0017612 | A1 | 1/2003 | Gerber |
| 2004/0081623 | A1 | 4/2004 | Eriksen et al. |
| 2004/0206354 | A1 | 10/2004 | Fisher et al. |
| 2005/0124907 | A1 | 6/2005 | Kuck et al. |
| 2005/0165311 | A1 | 7/2005 | Porter et al. |
| 2005/0228337 | A1 | 10/2005 | Rasor et al. |
| 2005/0238727 | A1 | 10/2005 | Cagnoni |
| 2006/0239524 | A1 | 10/2006 | Desh et al. |
| 2006/0264755 | A1 | 11/2006 | Maltz et al. |
| 2007/0169779 | A1 | 7/2007 | Freeman |
| 2007/0259966 | A1 | 11/2007 | Cagnoni |
| 2007/0287897 | A1* | 12/2007 | Faris ............. A61B 5/0091 600/310 |
| 2007/0299136 | A1 | 12/2007 | Johnson |
| 2008/0058709 | A1 | 3/2008 | Da Silva Freitas |
| 2008/0171933 | A1 | 7/2008 | Li et al. |
| 2010/0086483 | A1 | 4/2010 | Belardinelli et al. |
| 2010/0240983 | A1 | 9/2010 | Jung et al. |
| 2010/0305459 | A1 | 12/2010 | Whitt et al. |
| 2014/0053837 | A1* | 2/2014 | Klein ................. 128/203.14 |
| 2014/0170069 | A1 | 6/2014 | Dharmakumar et al. |
| 2015/0196207 | A1 | 7/2015 | Friedrich et al. |
| 2016/0045841 | A1 | 2/2016 | Kaplan |
| 2018/0185519 | A1 | 7/2018 | Dharmakumar et al. |
| 2019/0038781 | A1 | 2/2019 | Dharmakumar et al. |

FOREIGN PATENT DOCUMENTS

| | | |
|---|---|---|
| CA | 2832851 A1 | 5/2015 |
| EP | 2704577 A1 | 3/2014 |
| WO | WO 200057776 | 10/2000 |
| WO | 2000/078774 A1 | 12/2000 |
| WO | 2001/064280 A1 | 9/2001 |
| WO | 2007/084264 A1 | 7/2007 |
| WO | WO 2008122056 | 10/2008 |
| WO | WO2010/033971 | 3/2010 |
| WO | WO 2010033971 | 3/2010 |
| WO | WO 2010141081 | 12/2010 |
| WO | WO 2012151583 | 11/2012 |

OTHER PUBLICATIONS

Ledingham et al., "The Effect of Hypercapnia on Myocardial Blood Flow and Metabolism", J. Physiol. (1970), 210, pp. 87-105. (Year: 1970).*

Prisman et al., "Comparison of the Effects of Independently-Controlled End-Tidal PCO2 and PO2 on Blood Oxygen Level-Dependent (BOLD) MRI", Journal of Magnetic Resonance Imaging 27; 2008: pp. 185-191. (Year: 2008).*

Kaufamnn et al., "Myocardial Blood Flow Measurement by PET: Technical Aspects and Clinical Applications", J Nucl Med. Jan. 2005;46(1): pp. 75-88. (Year: 2005).*

Schuster et al., "An isolated perfused pig heart model for the development, validation and translation of novel cardiovascular magnetic resonance techniques", Journal of Cardiovascular Magnetic Resonance 2010, 12:53, pp. 1-9 (Year: 2010).*

Case et al., "Relative Effect of CO2 on Canine Coronary Vascular Resistance", Circ Res. Mar. 1978;42(3): pp. 410-418. (Year: 1978).*

Bruyne et al., "Coronary Flow Reserve Calculated From Pressure Measurements in Humans Validation With Positron Emission Tomography", Circulation. Mar. 1994;89(3): pp. 1013-1022. (Year: 1994).*

Araujo et al., "Noninvasive Quantification of Regional Myocardial Blood Flow in Coronary Artery Disease With Oxygen-15-Labeled Carbon Dioxide Inhalation and Positron", Circulation vol. 83, No. Mar. 3, 1991, pp. 875-885 (Year: 1991).*

ISR for PCT/US2012/036813, dated Jul. 18, 2012, 3 pages.

Written Opinion for PCT/US2012/036813, dated Jul. 18, 2012, 5 pages.

IPRP for PCT/US2012/036813, dated Jul. 18, 2012, 15 pages.

Back et al.. Angiography with Carbon Dioxide (CO2), Surgical Clinics of North America, vol. 78, Issue 4, pp. 575-591, Aug. 1, 1998 Abstract.

Final Office Action on co-pending US application (U.S. Appl. No. 14/075,918) dated Feb. 8, 2017.

Non-Final Office Action on co-pending US application (U.S. Appl. No. 14/075,918) dated May 2, 2016.

Baddeley, HI, et al. "Gas exchange parameters in radiotherapy patients during breathing of 2%, 3.5% and 5% carbogen gas mixtures." The British journal of radiology 73.874 (2000): 1100-1104.

CIPO, Examination Report, dated Dec. 20, 2018, re Canadian Patent Application No. 2845308.

CIPO, Examination Report, dated Sep. 24, 2019, re Canadian Patent Application No. 2832851.

Eckenhoff, J. E. et al. "The coronary circulation in the dog." American Journal of Physiology—Legacy Content 148.3 (1947): 582-596.

EPO, Communication pursuant to Article 94(3) EPC, dated Apr. 23, 2019, re European Patent Application No. 16835871.1.

EPO, Communication pursuant to Article 94(3) EPC, dated May 23, 2019, re European Patent Application No. 12779635.7.

EPO, Supplemental European Search Report, dated Apr. 9, 2019, re European Patent Application No. 16845248.0.

EPO, Supplementary European Search Report, dated Jul. 17, 2018, re European Patent Application No. 16835871.1.

Feigl, E. O. "Coronary physiology." Physiological reviews 63.1 (1983): 1-205.

Foster RS and Blaine J, (1977), 'Urban Tree Survival: Trees in the Sidewalk,' J Arboricult, 4(1):14-7.

(56) References Cited

OTHER PUBLICATIONS

International Search Report on corresponding PCT application (PCT/US2012/036813) from International Searching Authority (USPTO) dated Aug. 7, 2012.
Ledingham, I. McA, et al. "The effect of hypercapnia on myocardial blood flow and metabolism." The Journal of Physiology 210.1 (1970): 87.
Momen, Afsana, et al. "Coronary blood flow responses to physiological stress in humans." Am J Physiol Heart Circ Physiol 296 (2009): H854-H861.
Scheuer J. "The effects of respiratory and metabolic alkalosis on coronary flow, hemodynamics and myocardial carbohydrate metabolism." Cardiology 52.5 (1968): 275-286.
Written Opinion on corresponding PCT application (PCT/US2012/036813) from International Searching Authority (USPTO) dated Aug. 7, 2012.
U.S. Appl. No. 15/672,162, Assessment of Coronary Heart Disease With Carbon Dioxide, filed Aug. 8, 2017.
U.S. Appl. No. 15/910,718, Assessment of Coronary Heart Disease With Carbon Dioxide, filed Mar. 2, 2018.
Dutton, et al., Carbon Dioxide and Liver Blood Flow, Bull. Europ. Physiopath. Resp., 1976, vol. 12, pp. 265-272.
Foex et al., Effects of CO2 on the Systemic and Coronary Circulations and on Coronary Sinus Blood Gas Tensions, Bull. Europ Physiopath. Resp., 1979, vol. 15, pp. 625-638.
Kashiba et al., From O2 to H2S: A Landscape View of Gas Biology, Kieo J. Med, 2002, vol. 51(1), pp. 1-10.
Kisilevsky et al., Concentration-Dependent Vasoconstrictive Effect of Hyperoxia on Hypercarbia-Dilated Retinal Arterioles, Microvascular Research, 2008, vol. 75, pp. 263-268.
van den Elshout et al., Effects of Hypercapnia and Hypocapnia on Respiratory Resistence in Normal and Asthmatic Subjects, Thorax, 1991, vol. 46, pp. 28-32.
AU 2012250539 Examination Report dated Aug. 4, 2015, 3 pages.
CA 2845308 Office Action dated Oct. 25, 2018, 7 pages.
CA 2832851 A1 Office Action dated Aug. 31, 2020, 6 pages.
EP 12779635.7 Extended European Search Report dated Sep. 17, 2014, 7 pages.
Brandi et al., The Role of Carbon Dioxide Therapy in the Treatment of Chronic Wounds, In Vivo, 2010, vol. 24, pp. 223-226.
Wennmalm, A., Effect of Cigarette Smoking on Basal and Carbon Dioxide Stimulated Cerebral Blood Flow in Man, Clinical Physiology, 1982, vol. 2, pp. 529-535.

* cited by examiner

Statistics

Pair sample T test
2 groups; target CO2=30,40mmHg, CO2=50,60mmHg
Values are normalized by the average value of LCX from each dog
Samples from CO2 Ramp UP and Block gas paradigm
N=18,18

| LAD | | | RCA | | | LCX | | |
|---|---|---|---|---|---|---|---|---|
| Difference: -0.11153 | Mean | SD | Difference: -0.11963 | Mean | SD | Difference: -0.14268 | Mean | SD |
| Group1 | 0.71328 | 0.11988 | Group1 | 0.79736 | 0.14119 | Group1 | 0.92478 | 0.09077 |
| Group2 | 0.8248 | 0.07428 | Group2 | 0.91699 | 0.12568 | Group2 | 1.06746 | 0.08096 |
| t Statistic | DF | Prob>|t| | t Statistic | DF | Prob>|t| | t Statistic | DF | Prob>|t| |
| -3.67342 | 17 | 0.00186 | -4.98087 | 17 | 1.14036E-4 | -5.1445 | 17 | 8.10788E-5 |
| Significantly different | | | Significantly different | | | Significantly different | | |

| BLOOD | | | MUSCLE | | | AIR | | |
|---|---|---|---|---|---|---|---|---|
| Difference: -0.16278 | Mean | SD | Difference: -0.04141 | Mean | SD | Difference: -0.02098 | Mean | SD |
| Group1 | 2.88576 | 0.25895 | Group1 | 0.59048 | 0.15746 | Group1 | 0.21484 | 0.04433 |
| Group2 | 3.04854 | 0.29902 | Group2 | 0.6319 | 0.07306 | Group2 | 0.23582 | 0.05874 |
| t Statistic | DF | Prob>|t| | t Statistic | DF | Prob>|t| | t Statistic | DF | Prob>|t| |
| -2.00956 | 17 | 0.06063 | -1.42538 | 17 | 0.17215 | -1.85231 | 17 | 0.08143 |
| Not Significantly different | | | Not Significantly different | | | Not Significantly different | | |

* Mean hyperemic response (ramps and blocks) is approximately 16%

FIG. 9

Human Studies
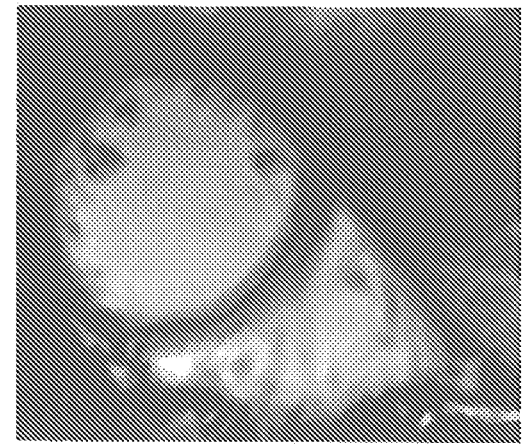
PaCO2: 35 mmHg
Signal:217.4
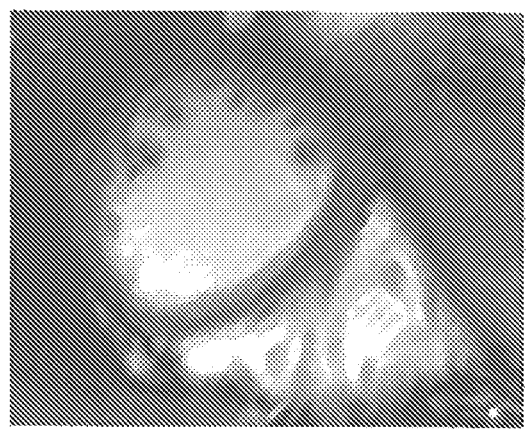
PaCO2: 45 mmHg
Signal:240.8
Hyperemic response of ~ 11% for a PaCO2 change of 10 mmHg (from 35 to 45 mmHg)
FIG. 11

ASSESSMENT OF CORONARY HEART DISEASE WITH CARBON DIOXIDE

CROSS-REFERENCE TO RELATED APPLICATIONS

This application is a National Phase of International Application No. PCT/US2012/036813, filed May 7, 2012, which designated the U.S. and that International Application was published under PCT Article 21(2) in English. The present application also includes a claim of priority under 35 U. S.C. §119(e) to U.S. Provisional Patent Application Ser. No. 61/482,956, filed May 5, 2011, the contents of each of which are incorporated herein by reference in their entirety.

STATEMENT REGARDING FEDERALLY SPONSORED RESEARCH OR DEVELOPMENT

This invention was made with government support under Grant No. HL091989 awarded by the National Institutes of Health. The government has certain rights in the invention.

FIELD OF INVENTION

The invention is directed to methods for detecting coronary heart disease using carbon dioxide ($CO_2$) to induce hyperemia and monitor vascular reactivity.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Coronary artery disease (CAD) leads to narrowing of the small blood vessels that supply blood and oxygen to the heart. Typically, atherosclerosis is the cause of CAD. As the coronary arteries narrow, blood flow to the heart can slow down or stop, causing, amongst other symptoms, chest pain (stable angina), shortness of breath and/or myocardial infarction. Numerous tests help diagnose CAD. Such tests include coronary angiography/arteriography, CT angiography, echocardiogram, electrocardiogram (ECG), electron-beam computed tomography (EBCT), magnetic resonance angiography, nuclear scan and exercise stress test. Functional assessment of the myocardium (for example the assessment of myocardium's oxygen status) requires that a patient's heart is stressed either via controlled exercise or pharmacologically.

Assessment of vascular reactivity in the heart is the hallmark of stress testing in cardiac imaging aimed at understanding ischemic heart disease. This is routinely done in Nuclear Medicine with radionuclide injection (such as Thallium) in conjunction with exercise to identify territories of the heart muscle that are subtended by a suspected narrowed coronary artery. In patients who are contraindicated for exercise stress-testing, this approach is typically used in conjunction with hyperemia inducing drugs, for example via adenosine infusion. Reduced coronary narrowing is expected to reduce hyperemic response and the perfusion reserve. Since nuclear methods are hampered by the need for radioactive tracers combined with limited imaging resolution, other imaging methods, such as ultrasound (using adenosine along with microbubble contrast) and MRI (also using adenosine and various conjugates of gadolinium (Gd) (first-pass perfusion) or alterations in oxygen saturation in response to hyperemia, also known as the Blood-Oxygen-Level-Dependent (BOLD) effect) are under clinical investigation. Nonetheless, in patients who are contraindicated for exercise stress-testing, currently all imaging approaches require adenosine to elicit hyperemia. However, adenosine has undesirable side effects (such as the feeling of "impending doom", bradycardia, arrhythmia, transient or prolonged episode of asystole, ventricular fibrillation (rarely), chest pain, headache, dyspnea, and nausea), making it less than favorable for initial or follow-up studies and many patients request that they do not undergo repeated adenosine stress testing. Nonetheless repeated stress testing is indicated in a significant patient population to assess the effectiveness of interventional or medical therapeutic regimens. In view of the side effects of hyperemia inducing drugs, there is a need for alternatives, which induce hyperemia in patients who are contraindicated for exercise stress-testing but do not cause the side effects caused by the existing hyperemia inducing drugs.

SUMMARY OF THE INVENTION

Applicants' invention is directed to the use of carbon dioxide to replace adenosine to induce hyperemia in subjects contra-indicated for exercise stress testing so as to diagnose coronary heart diseases but without the side effects of adenosine. In an embodiment, the $CO_2$ levels are altered while the $O_2$ levels are held constant.

The invention is directed to methods for diagnosing coronary heart disease in a subject in need thereof comprising administering an admixture comprising $CO_2$ to a subject to reach a predetermined $PaCO_2$ in the subject to induce hyperemia, monitoring vascular reactivity in the subject and diagnosing the presence or absence of coronary heart disease in the subject, wherein decreased vascular reactivity in the subject compared to a control subject is indicative of coronary heart disease.

The invention also provides a method for assessing hyperemic response in a subject in need thereof comprising administering an admixture comprising $CO_2$ to a subject to reach a predetermined $PaCO_2$ in the subject to induce hyperemia, monitoring vascular reactivity in the subject and assessing hyperemic response in the subject, wherein decreased vascular reactivity in the subject compared to a control subject is indicative of poor hyperemic response, thereby assessing hyperemic response in the subject in need thereof.

The invention further provides methods of producing coronary vasodilation in a subject in need thereof comprising administering an admixture comprising $CO_2$ to a subject to reach a predetermined $PaCO_2$ in the subject so as to produce coronary vasodilation, thereby producing coronary vasodilation in the subject.

The invention also provides methods from increasing sensitivity and specificity for BOLD MRI. The method includes administering an admixture comprising $CO_2$ to a subject to reach a predetermined $PaCO_2$ in the subject to induce hyperemia and imaging the myocardium using MRI to assess a hypermic response in response to a predetermined modulation in $PaCO_2$

BRIEF DESCRIPTION OF FIGURES

FIG. 9 is a table summarizing the statistical BOLD data associated with the $PaCO_2$ modulation in myocardial territories, blood, muscle and air, while $PaO_2$ is held constant.

FIG. 11 depicts the early findings of BOLD response to $PaCO_2$ in humans, while $PaO_2$ is held constant.

DETAILED DESCRIPTION OF THE INVENTION

Figure 1:
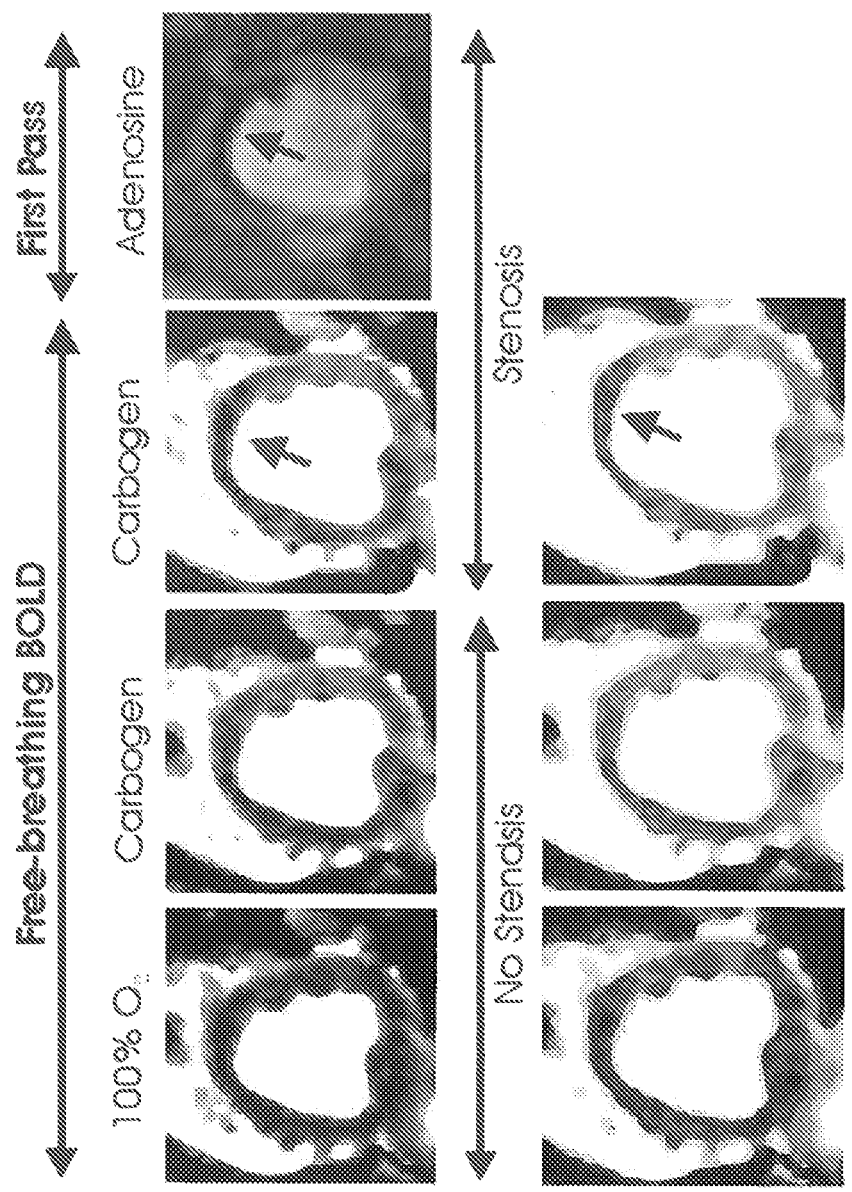
FIG. 1 depicts, in accordance with an embodiment of the present invention, the vascular reactivity in dogs as measured by the BOLD-effect using medical-grade Carbogen (5% $CO_2$ and 95% $O_2$) with and without coronary artery stenosis.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Carbogen" as used herein is an admixture of carbon dioxide and oxygen. The amounts of carbon dioxide and oxygen in the admixture may be determined by one skilled in the art. Medical grade carbogen is typically 5% $CO_2$ and 95% $O_2$. In various other embodiments, carbon dioxide is used to induce hyperemia may be an admixture of ranges including but not limited to 94% $O_2$ and 6% $CO_2$, 93% $O_2$ and 7% $CO_2$, 92% $O_2$ and 8% $CO_2$, 91% $O_2$ and 9% $CO_2$, 90% $O_2$ and 10% $CO_2$, 85% $O_2$ and 15% $CO_2$, 80% $O_2$ and 20% $CO_2$, 75% $O_2$ and 25% $CO_2$ and/or 70% $O_2$ and 30% $CO_2$.

"BOLD" as used herein refers to blood-oxygen-level dependence.

Current methods for inducing hyperemia in subjects include the use of compounds such as adenosine, analogs thereof and/or functional equivalents thereof. However, such compounds (for example, adenosine) have adverse side effects including bradycardia, arrhythmia, transient or prolonged episode of asystole, ventricular fibrillation (rarely), chest pain, headache, dyspnea, and nausea, making it less than favorable for initial or follow-up studies.

The invention described herein is directed to the use of $CO_2$ instead of hyperemia-inducing drugs, in view of their side effects, to assess myocardial response and risk of coronary artery diseases. To date, however, it has not been possible to independently control arterial $CO_2$ and $O_2$, hence direct association of the influence of partial pressure of $CO_2$ ($PaCO_2$) on coronary vasodilation has been difficult to determine. With the development of gas flow controller devices designed to control gas concentrations in the lungs and blood (for example, RespirACT™, Thornhill Research), it is now possible to precisely control the arterial $CO_2$, while, in some embodiments, holding $O_2$ constant. With such devices, the desired $PaCO_2$ changes are rapid (1-2 breaths) and are independent of minute ventilation. The inventors are the first adopters of such devices for the assessment of myocardial response to $CO_2$.

The claimed invention is believed to be the first to use modulation of $CO_2$ levels to show that the carbon dioxide has the same effect as the clinical dose of other hyperemia-inducing drugs such as adenosine but without the side effects. The inventors induce hyperemia by administering an admixture comprising a predetermined amount of $CO_2$ to a subject in need thereof to assess myocardial response, evaluate coronary artery disease and identify ischemic heart disease. In an embodiment, hyperemia is induced by independently altering the administered $CO_2$ level while holding oxygen ($O_2$) constant to assess myocardial response, evaluate coronary artery disease and identify ischemic heart disease. A subject's myocardial response after administration of $CO_2$ may be monitored using various imaging techniques such as MRI.

Cardiac Stress Testing

When exercise stress testing is contra-indicated (in nearly 50% of patients), every existing imaging modality uses adenosine (or its analogues such as dipyridamole or regadenoson) to induce hyperemia. However, as described above, adenosine or analogs thereof or functional equivalents thereof, are well known for their adverse side effects such as bradycardia, arrhythmia, transient or prolonged episode of asystole, ventricular fibrillation (rarely), chest pain, headache, dyspnea, and nausea, making it less than favorable for initial or follow-up studies. Direct measures of ischemic burden may be determined on the basis of single-photon emission computed tomography (SPECT/SPET), positron emission tomography (PET), myocardial contrast echocardiography (MCE), and first-pass perfusion magnetic resonance imaging (FPP-MRI). SPECT and PET use radiotracers as contrast agents. While SPECT and PET studies account for approximately 90% myocardial ischemia-testing studies, the sensitivity and specificity for both methods combined for the determination of severe ischemia is below 70%. Both MCE and FPP-MRI are relatively newer approaches that require the use of exogenous contrast media and intravenous pharmacological stress agent (adenosine), both carrying significant risks and side effects in certain patient populations.

BOLD-MRI

An alternate method, BOLD (Blood-Oxygen-Level-Dependent) MRI, relies on endogenous contrast mechanisms (changes in blood oxygen saturation, % $O_2$) to identify ischemic territories. The potential benefits of BOLD MRI for detecting global or regional myocardial ischemia due to coronary artery disease (CAD) were demonstrated by the inventors and others at least a decade ago. Although a number of pilot clinical studies have demonstrated the feasibility of using BOLD MRI for identifying clinically significant myocardial ischemia due to CAD, the method is inherently limited by sensitivity and specificity due to low BOLD contrast-to-noise ratio (CNR). The repeatability of BOLD MRI using $CO_2$ provides the means to improve sensitivity and specificity, which is not possible using adenosine or analogs thereof.

The invention provides a method for increasing the sensitivity and specificity of BOLD MRI. The method includes administering an admixture comprising of $CO_2$ to the subject in need thereof to induce hyperemia and imaging the myocardium using MRI to assess a hypermic response in response to a predetermined modulation in $PaCO_2$.

The proposed method utilizes (i) an individualized targeted change in arterial partial pressure of $CO_2$ ($PaCO_2$) as the non-invasive vasoactive stimulus, (ii) fast, high-resolution, 4D BOLD MRI at 3 T and (iii) statistical models (for example, the generalized linear model (GLM) theory) to derive statistical parametric maps (SPM) to reliably detect and quantify the prognostically significant ischemic burden through repeated measurements (i.e. in a data-driven fashion).

The method for increasing the sensitivity and specificity of BOLD MRI comprises (i) obtaining free-breathing cardiac phase-resolved 3D myocardial BOLD images (under different $PaCO_2$ states established via inhalation of an admixture of gases comprising of $CO_2$); (ii) registering and segmenting the images to obtain the myocardial dynamic volume and (iii) identifying ischemic territory and quantify image volume.

Obtaining the Images

The first step in increasing the sensitivity and specificity of BOLD MRI is to obtain free-breathing cardiac phase resolved 3D myocardial BOLD images. Subjects are placed on the MRI scanner table, ECG leads are placed, and necessary surface coils are positioned. Subsequently their hearts are localized and the cardiac shim protocol is prescribed over the whole heart. K-space lines, time stamped for trigger time are collected using cine SSFP acquisition with image acceleration along the long axis. Central k-space lines corresponding to each cardiac phase will be used to derive the center of mass (COM) curves along the z-axis via 1-D fast Fourier transform (FFT). Based on the COM curves, the k-space lines from each cardiac phase will be sorted into 1-30 bins, each corresponding to a respiratory state with the first bin being the reference bin (end-expiration) and the last bin corresponding to end inspiration.

To minimize the artifacts from under sampling, the data will be processed with a 3D filter, followed by re-gridding the k-space lines, application of a spatial mask (to restrict the registration to region of the heart) and performing FFT to obtain the under sampled 3D image for each respiratory bin. Using the end-expiration image as the reference image, images from all bins (except bin 1) are registered using kits such as Insight Tool Kit (freely available from www.itk.org), or an equivalent software platform, in an iterative fashion and the transform parameters will be estimated for rotation, scaling, shearing, and translation of heart between the different respiratory bins. The k-space data will again be divided into 1 to 30 respiratory bins, re-gridded, transformed to the reference image (3D affine transform), summed together, and the final 3D image will be reconstructed. Imaging parameters may be TR=3.0 to 10 ms and flip angle=1° to 90°. In this fashion, 3D cine data under controlled $PaCO_2$ values (hypo- and hyper-carbic states) are collected.

Registration and Segmentation of Images

The next step in increasing the sensitivity and specificity of BOLD MRI is registration and segmentation of the images to obtain the myocardial dynamic volume. The pipeline utilizes MATLAB and C++ using the ITK framework or an equivalent software platform. The myocardial MR images obtained with repeat $CO_2$ stimulation blocks will be loaded in MATLAB (or an equivalent image processing platform) and arranged in a four-dimensional (4D) matrix, where the first 3 dimensions represent volume (voxels) and the fourth dimension is time (cardiac phase). Subsequently, each volume is resampled to achieve isotropic voxel size. End-systole (ES) are identified for each stack based on our minimum cross-correlation approach. A 4D non-linear registration algorithm is used to find voxel-to-voxel correspondences (deformation fields) across all cardiac phases. Using the recovered deformation, all cardiac phases are wrapped to the space of ES, such that all phases are aligned to ES. Recover the transformations across all ES images from repeat $CO_2$ blocks and bring them to the same space using a diffeomorphic volume registration tool, such as ANTs. Upon completion, all cardiac phases from all acquisitions will be spatially aligned to the space of ES of the first acquisition (used as reference) and all phase-to-phase deformations and acquisition-to-acquisition transformations will be known. An expert delineation of the myocardium in the ES of the first (reference) acquisition will then be performed. Based on the estimated deformation fields and transformations, this segmentation is propagated to all phases and acquisitions, resulting in fully registered and segmented myocardial dynamic volumes.

Image Analysis to Identify and Quantify Ischemic Territories

The final step needed for increasing the sensitivity and specificity of BOLD MRI is identifying ischemic territory and quantify image volume. Since BOLD responses are optimally observed in systolic frames, only L systolic cardiac volumes (centered at ES) are retained from each fully registered and segmented 4D BOLD MR image set obtained above. Only those voxels contained in the myocardium are retained and the corresponding RPP (rate-pressure-product) and $PaCO_2$ are noted. Assuming N acquisitions per $CO_2$ state (hypocarbic or hypercarbic) and K, $CO_2$ stimulation blocks, and each cardiac volume consists of n×m×p (×=multiplication) isotropic voxels, build a concatenated fully registered 4D dataset consisting of n×m×p×t pixels, where x=multiplication and t=L×K×N, and export this dataset in NIFTI (or an equivalent) format using standard tools. The 4D dataset is loaded into a voxel-based statistical model fitting (such as FSL-FEAT developed for fMRI), to fit the model for each voxel. The statistical analysis outputs a P-statistic volume, i.e., the SPM, where for each voxel in the myocardium the p-value of the significance of the correlation to the model is reported. The statistical parametric maps (SPM) are thresholded by identifying the voxels that have p<0.05. Those voxels are identified as hyperemic for responding to the $CO_2$ stimulation. The total number of hyperemic voxels ($V_H$) are counted and their relative volume ($V_{RH}=V_H$/total voxels in myocardium) is determined. The voxels that do not respond to $CO_2$ stimulation (on SPM) are identified as ischemic and used to generate a binary 3D map of ischemic voxels (3D-$ISCH_{map}$). In addition, total ischemic voxels ($V_I$) and the relative ischemic volume ($V_{RI}=V_I$/total myocardial voxels) are determined.

The above methods provide ischemic volumes that can be reliably identified on the basis of statistical analysis applied to repeatedly acquire 4D BOLD images under precisely targeted changes in $PaCO_2$. These volumes are closely related to the clinical index of fractional flow reserve FFR.

FFR

An additional method, fractional flow reserve (FFR) is used in coronary catheterization to measure pressure differences across a coronary artery stenosis to determine the likelihood that the stenosis impedes oxygen delivery to the heart muscle (myocardial ischemia). Fractional flow reserve measures the pressure behind (distal to) a stenosis relative to the pressure before the stenosis, using adenosine or papaverine to induce hyperemia. A cut-off point of 0.75 to 0.80 has been used wherein higher values indicate a non-significant stenosis and lower values indicate a significant lesion. FFR, determined as the relative pressure differences across the stenotic coronary artery has emerged as the new standard for determining clinically significant ischemia (FFR≤0.75). However, it is invasive, expensive, and exposes the patient to ionizing radiation and the side-effects of the use of adenosine. In view of the side-effects of adenosine discussed above, Applicants propose using carbon dioxide instead of adenosine to induce hyperemia, by administering to a subject an admixture comprising $CO_2$ to reach a predetermined $PaCO_2$ in the subject to induce hyperemia. In some embodiments, the admixture comprises any one or more of carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ or $N_2$ in an admixture are changed or held constant as would be readily apparent to a person having ordinary skill in the art.

METHODS OF THE INVENTION

The invention is directed to methods for diagnosing coronary heart disease in a subject in need thereof comprising administering an admixture comprising $CO_2$ to a subject to reach a predetermined $PaCO_2$ in the subject to induce hyperemia, monitoring vascular reactivity in the subject and diagnosing the presence or absence of coronary heart disease in the subject, wherein decreased vascular reactivity in the subject compared to a control subject is indicative of coronary heart disease. In an embodiment, $CO_2$ is administered via inhalation. In another embodiment, $CO_2$ levels are altered while the $O_2$ levels remain unchanged so that the $PaCO_2$ is changed independently of the $O_2$ level. In a further embodiment, vascular reactivity is monitored using imaging techniques deemed appropriate by one skilled in the art, including but not limited to any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), electron spin resonance (ESR) and/or any combination of the imaging modalities such as (PET/MR), PET/CT, and/or SPECT/MR. In an embodiment, vascular reactivity is monitored using free-breathing BOLD MRI. In some embodiments, the admixture comprises any one or more of carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ or $N_2$ in an admixture are changed or held constant as would be readily apparent to a person having ordinary skill in the art.

The invention also provides a method for assessing hyperemic response in a subject in need thereof comprising administering an admixture comprising $CO_2$ to a subject to reach a predetermined $PaCO_2$ in the subject to induce hyperemia, monitoring vascular reactivity in the subject and assessing hyperemic response in the subject, wherein decreased vascular reactivity in the subject compared to a control subject is indicative of poor hyperemic response, thereby assessing hyperemic response in the subject in need thereof. This method may also be used to assess organ perfusion and assess vascular reactivity. In an embodiment, $CO_2$ is administered via inhalation. In another embodiment, $CO_2$ levels are altered while the $O_2$ levels remain unchanged so that the $PaCO_2$ is changed independently of the $O_2$ level. In a further embodiment, vascular reactivity is monitored using imagining techniques deemed appropriate by one skilled in the art, including but not limited to any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), electron spin resonance (ESR) and/or any combination of the imaging modalities such as (PET/MR), PET/CT, and/or SPECT/MR. In an embodiment, vascular reactivity is monitored using free-breathing BOLD MRI. In some embodiments, the admixture comprises any one or more of carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ or $N_2$ in an admixture are changed or held constant as would be readily apparent to a person having ordinary skill in the art.

The invention is further directed to methods for producing coronary vasodilation in a subject in need thereof comprising providing a composition comprising $CO_2$ and administering the composition comprising $CO_2$ to a subject to reach a predetermined $PaCO_2$ in the subject so as to produce coronary vasodilation in the subject, thereby producing coronary vasodilation in the subject. In an embodiment, $CO_2$ is administered via inhalation. In another embodiment, $CO_2$ levels are altered while the $O_2$ levels remain unchanged so that the $PaCO_2$ is changed independently of the $O_2$ level. In a further embodiment, vascular reactivity is monitored using imagining techniques deemed appropriate by one skilled in the art, including but not limited to any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), electron spin resonance (ESR) and/or any combination of the imaging modalities such as (PET/MR), PET/CT, and/or SPECT/MR. In an embodiment, vascular reactivity is monitored using free-breathing BOLD MRI. In some embodiments, the admixture comprises any one or more of carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ or $N_2$ in an admixture are changed or held constant as would be readily apparent to a person having ordinary skill in the art.

The invention also provides a method for assessing tissue and/or organ perfusion in a subject in need thereof comprising administering an admixture comprising $CO_2$ to a subject to reach a predetermined $PaCO_2$ in the subject to induce hyperemia, monitoring vascular reactivity in the tissue and/or organ and assessing tissue and/or organ perfusion by assessing the hyperemic response in the subject, wherein decreased vascular reactivity in the subject compared to a control subject is indicative of poor hyperemic response and therefore poor tissue and/or organ perfusion. In an embodiment, $CO_2$ is administered via inhalation. In another embodiment, $CO_2$ levels are altered while the $O_2$ levels remain unchanged so that the $PaCO_2$ is changed independently of the $O_2$ level. In a further embodiment, vascular reactivity is monitored using imagining techniques deemed appropriate by one skilled in the art, including but not limited to any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), electron spin resonance (ESR) and/or any combination of the imaging modalities such as (PET/MR), PET/CT, and/or SPECT/MR. In an embodiment, vascular reactivity is monitored using free-breathing BOLD MRI. In some embodiments, the admixture comprises any one or more of carbon dioxide, oxygen and nitrogen; carbon dioxide and oxygen; carbon dioxide and nitrogen; or carbon dioxide alone. In one embodiment, the amounts of $CO_2$ and $O_2$ administered are both altered. In another embodiment, the amount of $CO_2$ administered is altered to a predetermined level while the amount of $O_2$ administered is held constant. In various embodiments, the amounts of any one or more of $CO_2$, $O_2$ or $N_2$ in an admixture are changed or held constant as would be readily apparent to a person having ordinary skill in the art.

In some embodiments, the admixture comprising $CO_2$ is administered at high doses for short duration or at low doses for longer durations. For example, administering the admixture comprising $CO_2$ at high doses of $CO_2$ for a short duration comprises administering any one or more of 40 mmHg to 45 mmHg, 45 mmHg to 50 mmHg, 50 mmHg to 55 mmHg, 55 mmHg $CO_2$ to 60 mm Hg $CO_2$, 60 mmHg $CO_2$ to 65 mm Hg $CO_2$, 65 mmHg $CO_2$ to 70 mm Hg $CO_2$, 70 mmHg $CO_2$ to 75 mm Hg $CO_2$, 75 mmHg $CO_2$ to 80 mm Hg $CO_2$, 80 mmHg $CO_2$ to 85 mm Hg $CO_2$ or a combination thereof, for about 20 minutes, 15 minutes, 10 minutes, 9 minutes, 8 minutes, 7 minutes, 6 minutes, 5 minutes, 4 minutes, 3 minutes, 2 minutes, 1 minute or a combination thereof. In various embodiments, the predetermined levels of $CO_2$ are administered so that the arterial level of $CO_2$ reaches the $PaCO_2$ of any one or more of the above ranges.

For example, administering low doses of predetermined amounts of $CO_2$ for a longer duration comprises administering the predetermined amount of $CO_2$ at any one or more of about 30 mmHg $CO_2$ to about 35 mmHg $CO_2$, about 35 mmHg $CO_2$ to about 40 mmHg $CO_2$, about 40 mmHg $CO_2$ to about 45 mmHg $CO_2$ or a combination thereof for any one or more of about 20 to 24 hours, about 15 to 20 hours, about 10 to 15 hours, about 5 to 10 hours, about 4 to 5 hours, about 3 to 4 hours, about 2 to 3 hours, about 1 to 2 hours, or a combination thereof, before inducing hyperemia. In various embodiments, the predetermined levels of $CO_2$ are administered so that the arterial level of $CO_2$ reaches the $PaCO_2$ of any one or more of the above ranges.

In one embodiment, $CO_2$ is administered in a stepwise manner. In another embodiment, administering carbon dioxide in a stepwise manner includes administering carbon dioxide in 5 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In another embodiment, administering carbon dioxide in a stepwise manner includes administering carbon dioxide in 10 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 20 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 30 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 40 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

In a further embodiment, administering carbon dioxide in a stepwise manner includes administering carbon dioxide in 50 mmHg increments in the range of any one or more of 10 mmHg to 100 mmHg $CO_2$, 20 mmHg to 100 mmHg $CO_2$, 30 mmHg to 100 mmHg $CO_2$, 40 mmHg to 100 mmHg $CO_2$, 50 mmHg to 100 mmHg $CO_2$, 60 mmHg to 100 mmHg $CO_2$, 10 mmHg to 90 mmHg $CO_2$, 20 mmHg to 90 mmHg $CO_2$, 30 mmHg to 90 mmHg $CO_2$, 40 mmHg to 90 mmHg $CO_2$, 50 mmHg to 90 mmHg $CO_2$, 60 mmHg to 90 mmHg $CO_2$, 10 mmHg to 80 mmHg $CO_2$, 20 mmHg to 80 mmHg $CO_2$, 30 mmHg to 80 mmHg $CO_2$, 40 mmHg to 80 mmHg $CO_2$, 50 mmHg to 80 mmHg $CO_2$, 60 mmHg to 80 mmHg $CO_2$, 10 mmHg to 70 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 70 mmHg $CO_2$, 30 mmHg to 70 mmHg $CO_2$, 40 mmHg to 70 mmHg $CO_2$, 50 mmHg to 70 mmHg $CO_2$, 60 mmHg to 70 mmHg $CO_2$, 10 mmHg to 60 mmHg $CO_2$, 20 mmHg to 60 mmHg $CO_2$, 30 mmHg to 60 mmHg $CO_2$, 40 mmHg to 60 mmHg $CO_2$ or 50 mmHg to 60 mmHg $CO_2$. In various embodiments, the predetermined levels of $CO_2$ are administered so that the arterial level of $CO_2$ reaches the $PaCO_2$ of any one or more of the above ranges.

Other increments of carbon dioxide to be administered in a stepwise manner will a readily apparent to a person having ordinary skill in the art.

In a further embodiment, predetermined amount of $CO_2$ is administered in a block manner. Block administration of carbon dioxide comprises administering carbon dioxide in alternating amounts over a period of time. In alternating amounts of $CO_2$ comprises alternating between any of 20 mmHg and 40 mmHg, 30 mmHg and 40 mmHg, 20 mmHg and 50 mmHg, 30 mmHg and 50 mmHg, 40 mmHg and 50 mmHg, 20 mmHg and 60 mmHg, 30 mmHg and 60 mmHg, 40 mmHg and 60 mmHg, or 50 mmHg and 60 mmHg. In various embodiments, the predetermined levels of $CO_2$ are administered so that the arterial level of $CO_2$ reaches the $PaCO_2$ of any one or more of the above ranges. Other amounts of carbon dioxide to be used in alternating amounts over a period of time will be readily apparent to a person having ordinary skill in the art.

In one embodiment, vascular reactivity may be measured by characterization of Myocardial Perfusion Reserve, which is defined as a ratio of Myocardial Perfusion at Stress to Myocardial Perfusion at Rest. In healthy subjects the ratio may vary from 5:1 to 6:1. The ratio diminishes with disease. A decrease in this ratio to 2:1 from the healthy level is considered the clinically significant and indicative of poor vascular reactivity.

In another embodiment, vascular reactivity may be measured via differential absolute perfusion, which may be obtained using imaging methods such as first pass perfusion, SPECT/PET, CT perfusion or echocardiography in units of ml/sec/g of tissue.

In an embodiment the $CO_2$ gas is administered via inhalation. $CO_2$ may be administered using, for example, RespirACT™ technology from Thornhill Research. In various embodiments, $CO_2$ is administered for 1-2 minutes, 2-4 minutes, 4-6 minutes, 6-8 minutes, 8-10 minutes, 10-12 minutes, 12-14 minutes, 14-16 minutes, 16-18 minutes and/or 18-20 minutes. In a preferred embodiment, $CO_2$ is administered for 4-6 minutes.

In an additional embodiment $CO_2$ is administered for an amount of time it takes for the arterial $PaCO_2$ (partial pressure of carbon dioxide) to reach 50-60 mmHg from the standard levels of 30 mmHg during $CO_2$-enhanced imaging.

In one embodiment, carbon dioxide used to induce hyperemia is medical-grade carbogen which is an admixture of 95% $O_2$ and 5% $CO_2$. In various other embodiments, carbon dioxide is used to induce hyperemia may be an admixture of ranges including but not limited to 94% $O_2$ and 6% $CO_2$, 93% $O_2$ and 7% $CO_2$, 92% $O_2$ and 8% $CO_2$, 91% $O_2$ and 9% $CO_2$, 90% $O_2$ and 10% $CO_2$, 85% $O_2$ and 15% $CO_2$, 80% $O_2$ and 20% $CO_2$, 75% $O_2$ and 25% $CO_2$ and/or 70% $O_2$ and 30% $CO_2$.

In another embodiment, vascular reactivity and/or vasodilation are monitored using any one or more of positron emission tomography (PET), single photon emission computed tomography/computed tomography (SPECT), computed tomography (CT), magnetic resonance imaging (MRI), functional magnetic resonance imaging (fMRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), electron spin resonance (ESR) and/or any combination of the imaging modalities such as (PET/MR), PET/CT, and/or SPECT/MR In an embodiment, vascular reactivity is monitored using free-breathing BOLD MRI.

Imaging techniques using carbon dioxide involve a free-breathing approach so as to permit entry of $CO_2$ into the subject's system. In an embodiment, the subjects include mammalian subjects, including, human, monkey, ape, dog, cat, cow, horse, goat, pig, rabbit, mouse and rat. In a preferred embodiment, the subject is human.

ADVANTAGES OF THE INVENTION

The methods described herein to functionally assess the oxygen status of the myocardium include administering an effective amount of $CO_2$ to the subject in need thereof. In an embodiment, the $O_2$ level is held constant while the $CO_2$ level is altered so as to induce hyperemia. Applicants herein show the vascular reactivity in subjects in response to changes in $PaCO_2$. The existing methods use adenosine, dipyridamole, or regadenoson which have significant side-effects described above. As described in the Examples below, $CO_2$ is at least just as effective as the existing methods (which use, for example, adenosine) but without the side effects.

The use of $CO_2$ provides distinct advantages over the use of, for example, adenosine. Administering $CO_2$ is truly non-invasive because it merely involves inhaling physiologically sound levels of $CO_2$. The instant methods are simple, repeatable and fast and most likely have the best chance for reproducibility. Not even breath-holding is necessary during acquisition of images using the methods described herein. The instant methods are also highly cost-effective as no pharmacological stress agents are required, cardiologists may not need to be present during imaging and rapid imaging reduces scan times and costs.

Further, the improved BOLD MRI technique described above provides a non-invasive and reliable determination of ischemic volume (no radiation, contrast-media, or adenosine) and other value-added imaging biomarkers from the same acquisition (Ejection Fraction, Wall Thickening). Additionally, the subject does not experience adenosine-related adverse side effects and thus greater patient tolerance for repeat ischemia testing. There is a significant cost-savings from abandoning exogenous contrast media and adenosine/regadenoson. Moreover, the proposed BOLD MRI paradigm will be accompanied by significant technical advances as well: (i) a fast, high-resolution, free-breathing 4D SSFP MRI at 3 T, that can impact cardiac MRI in general; (ii) Repeated stimulations of the heart via precisely targeted changes in $PaCO_2$; and (iii) adoption of sophisticated analytical methods employed in the brain to the heart.

EXAMPLES

All imaging studies were performed in instrumented animals with a Doppler flow probe attached to the LAD coronary arteries for measurement of flow changes in response to $CO_2$ and clinical dose of adenosine. In these studies, $CO_2$ and $O_2$ delivery were tightly controlled using Respiract. $CO_2$ values were incremented in steps of 10 mmHg starting from 30 mmHg to 60 mmHg and were ramped down in decrements of 10 mmHg. At each $CO_2$ level, free-breathing and cardiac gated blood-oxygen-level-dependent (BOLD) acquisitions were prescribed at mid diastole and Doppler flow velocities were measured. Similar acquisitions were also performed with block sequences of $CO_2$ levels; that is, $CO_2$ levels were alternated between 40 and 50 mmHg and BOLD images (and corresponding Doppler flow velocities) were acquired at each $CO_2$ level to assess the reproducibility of the signal changes associated with different $CO_2$ levels. Each delivery of $CO_2$ using Respiract were made in conjunction with arterial blood draw to determine the arterial blood $CO_2$ levels. Imaging-based demonstration of myocardial hyperemic response to changes in $PaCO_2$ was shown in health human volunteers with informed consent.

Example 1

The inventor has shown that $CO_2$ can increase myocardial perfusion by a similar amount, as does adenosine in canine models. The inventor has also shown that in the setting of coronary artery narrowing, it is possible to detect regional variations in hyperemic response with the use of MRI by detecting signal changes in the myocardium due to changes in oxygen saturation (also known as the BOLD effect) using a free-breathing BOLD MRI approach.

As show in FIG. 1, the inventor found a 20% BOLD signal increase (hyperemic response) with medical-grade carbogen breathing in the absence of stenosis in dogs. With a severe stenosis, the hyperemic response was significantly reduced in the LAD (left anterior descending) territory but the other regions showed an increase in signal intensity (as observed with adenosine). First-pass perfusion images acquired with adenosine under severe stenosis (in the same slice position and trigger time) is also shown for comparison. Heart rate increase of around 5-10% and a drop in blood pressure (measured invasively) by about 5% was also observed in this animal under carbogen. All acquisitions were navigator gated T2-prep 2D SSFP (steady-state free precession) and triggered at mid/end diastole (acquisition window of 50 ms). To date 10 dogs have been studied with medical-grade carbogen and have yielded highly reproducible results.

In detail, the color images (lower panel of FIG. 1) are color-coded to the signal intensities of grayscale images (above). The darker colors (blue/black) represent territories of baseline myocardial oxygenation and the brighter regions represent those regions that are hyperemic. On average the signal difference between a dark blue (low signal) and orange color (high signal) is about 20%. Note that in the absence of stenosis, as one goes from 100% $O_2$ to Carbogen, the BOLD signal intensity is elevated (second image from left) suggesting $CO_2$ based vasoreactivity of the myocardium. The dogs were instrumented with an occluder over the left-anterior descending (LAD) coronary artery. As the LAD is occluded, note that the region indicated by an arrow (i.e. approximately between 11 o'clock and 1-2 o'clock (region supplied by the LAD)) becomes darker (3rd image from left), suggesting that vasodilation is no longer possible or is reduced. The first pass image (obtained with adenosine stress following BOLD images) at the same stenosis level also shows this territory clearly. The inventor has also been comparing the epicardial flow enhancements in response to Carbogen (with ETCO2 reaching 48-50 mm Hg) against clinical dose of adenosine and the responses have been quite similar (~20% response).

Example 2

Co-Relation Between Inhaled $CO_2$ and Oxygen Saturation

Applicants assessed the difference between myocardial blood-oxygen-level dependent (BOLD) response under hypercarbia and normocarbia conditions in canines. The BOLD signal intensity is proportional to oxygen saturation.

Figure 2:
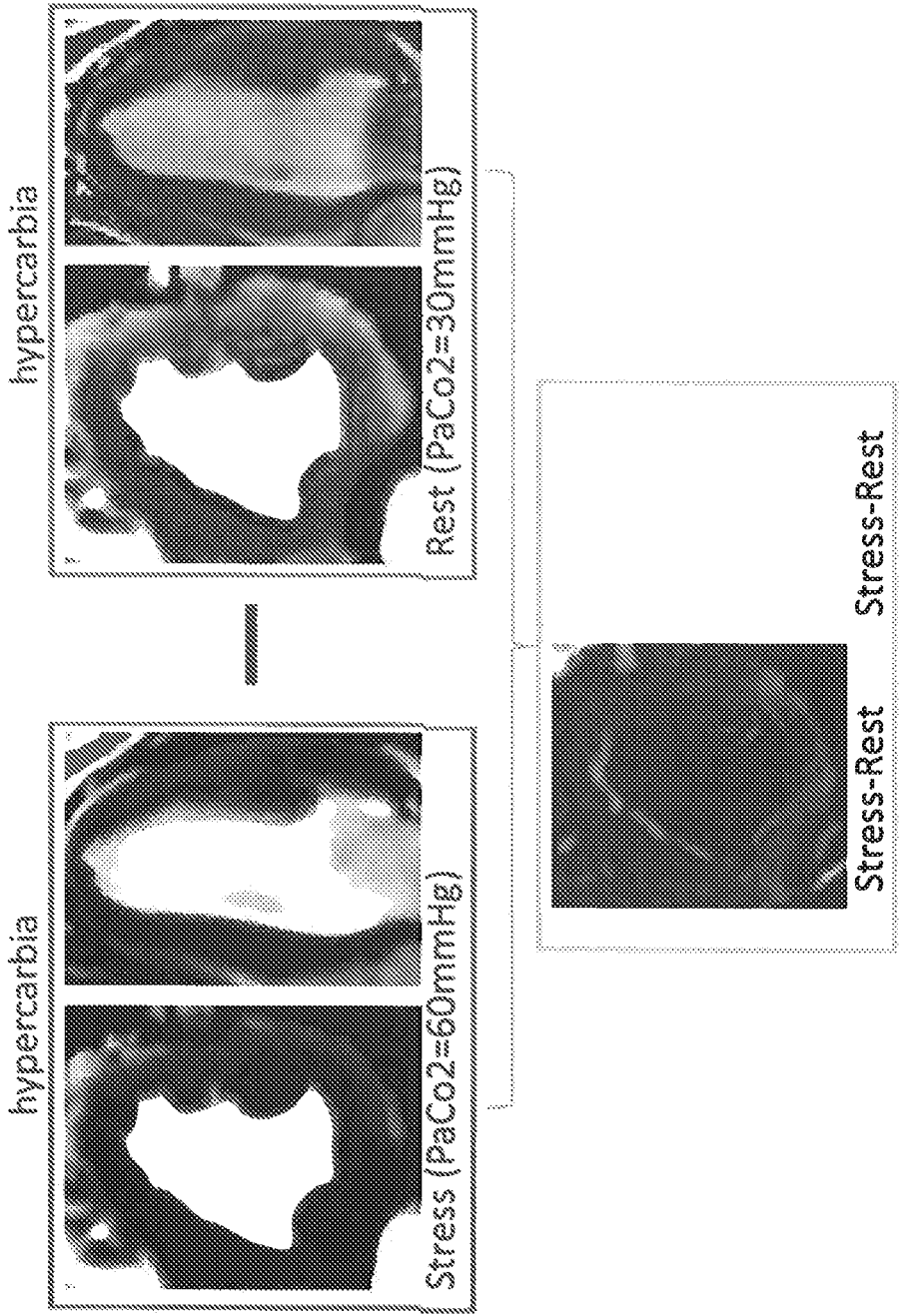
FIG. 2 depicts myocardial BOLD MRI with $CO_2$ in canines under normocarbic and hypercarbic conditions under free breathing conditions.

Top panels of FIG. 2 depict the myocardial response under hypercarbia (60 mm Hg) and normocarbia (30 mmHg) conditions and show an increase in BOLD signal intensity under hypercarbia condition. The lower panel depicts the difference as obtained by subtracting the signal under rest from that under stress. The myocardial BOLD signal difference between the two is depicted in grey and shows the responsiveness of canines to hypercarbia conditions.

Figure 3:
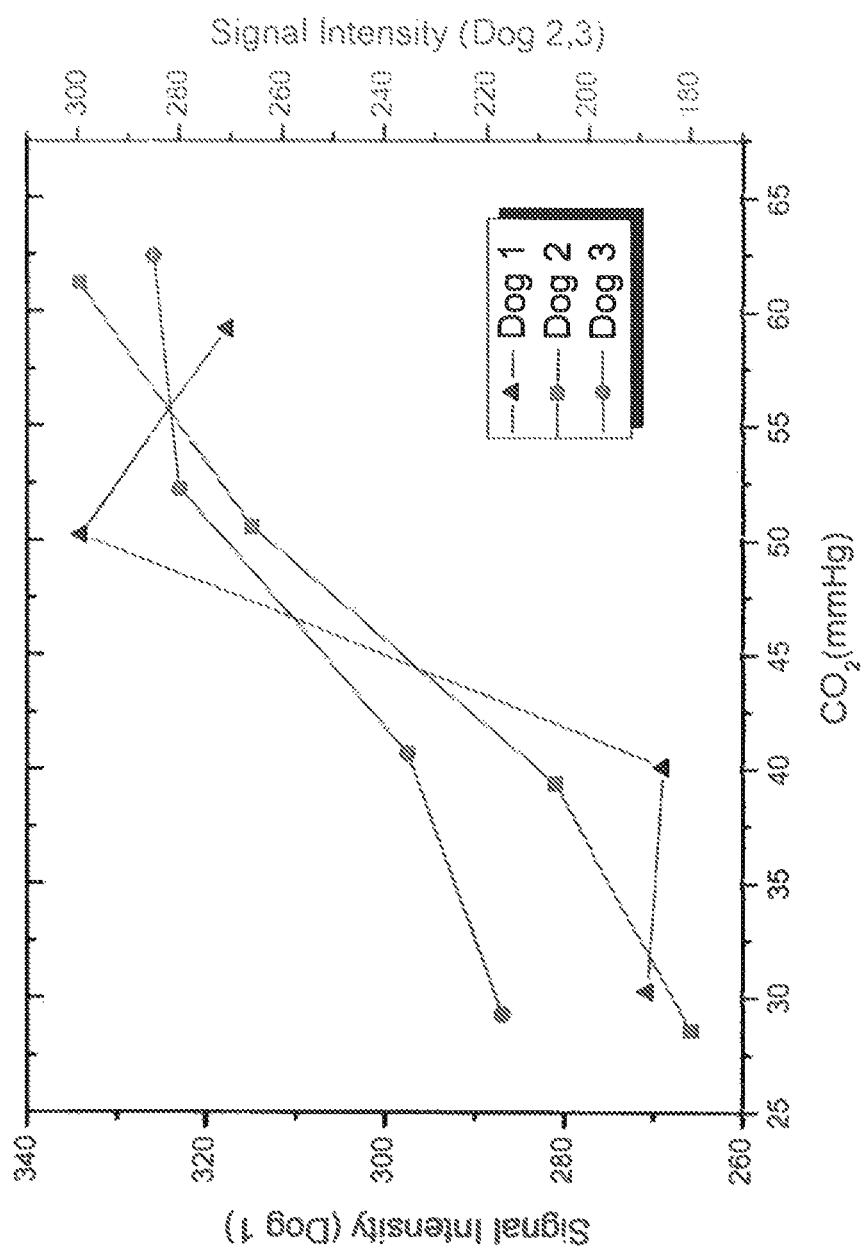
FIG. 3 depicts myocardial BOLD response to step-wise $PaCO_2$ ramp up in canines while holding basal $PaO_2$ constant.

Applicants further assessed the myocardial BOLD response to stepwise $CO_2$ increase (ramp-up) in canines. As shown in FIG. 3, as the amount of $CO_2$ administered increases, the BOLD signal intensity increases which is indicative of an increase in hyperemic response to increased uptake of $CO_2$ and oxygen saturation.

Figure 4:
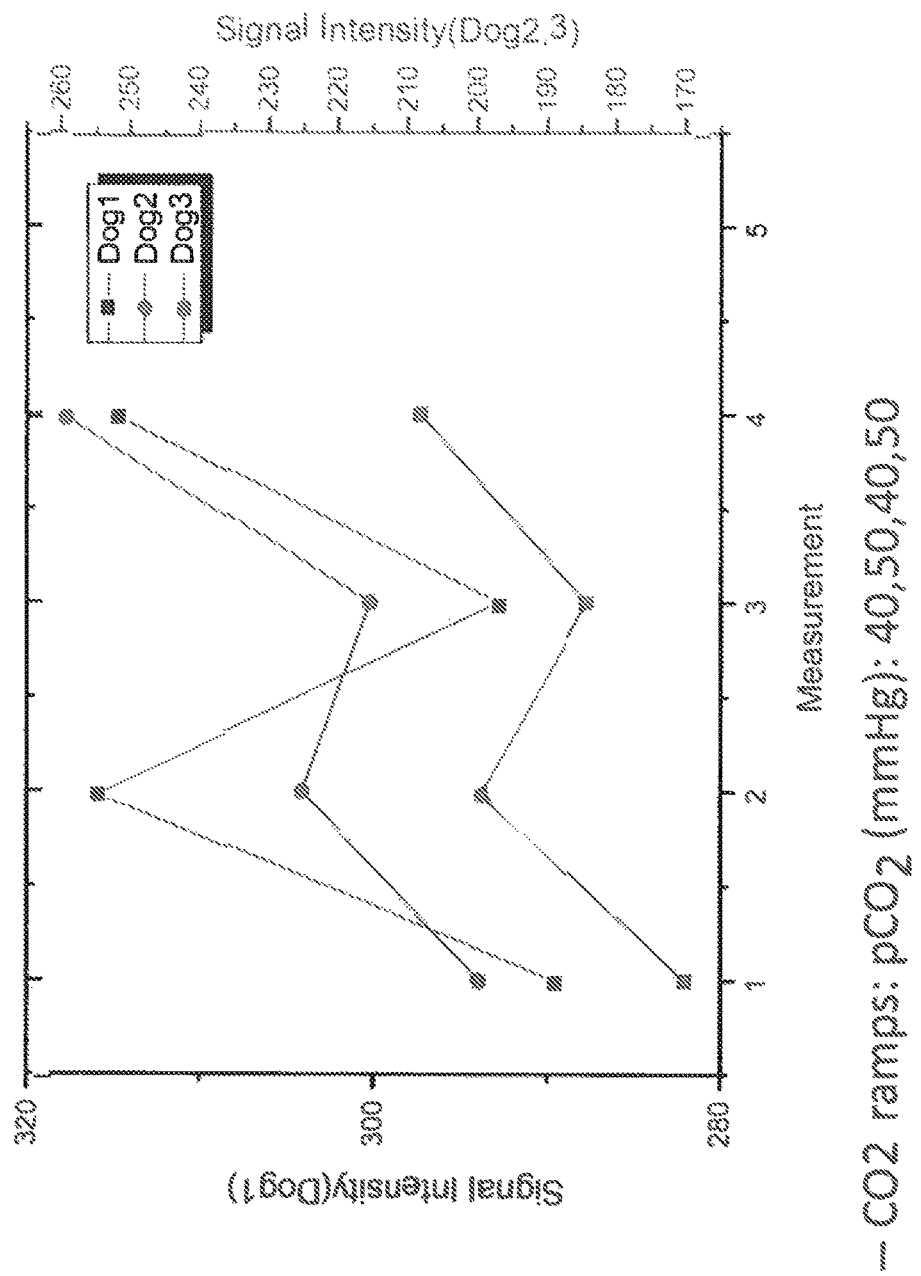
FIG. 4 depicts myocardial BOLD response to repeated (block) administration $CO_2$ response.

To further evaluate vascular reactivity and coronary response to $CO_2$, Applicants measured the myocardial BOLD signal in response to block increases of $CO_2$ in canines Specifically, the myocardial BOLD signal was measured as the amount of $CO_2$ administered to the canine subjects alternated between 40 mmHg $CO_2$ and 50 mmHg $CO_2$. As shown in FIG. 4, an increase in $CO_2$ level from 40 mmHg $CO_2$ to 50 mmHg $CO_2$ resulted in an increase in BOLD signal intensity and the subsequent decrease in $CO_2$ level to 40 mmHg resulted in a decreased BOLD signal. These results show a tight co-relation between administration of $CO_2$ and vascular reactivity and coronary response.

Example 3

Co-Relation Between the Amount of $CO_2$ Inhaled and Doppler Flow

Figure 5:
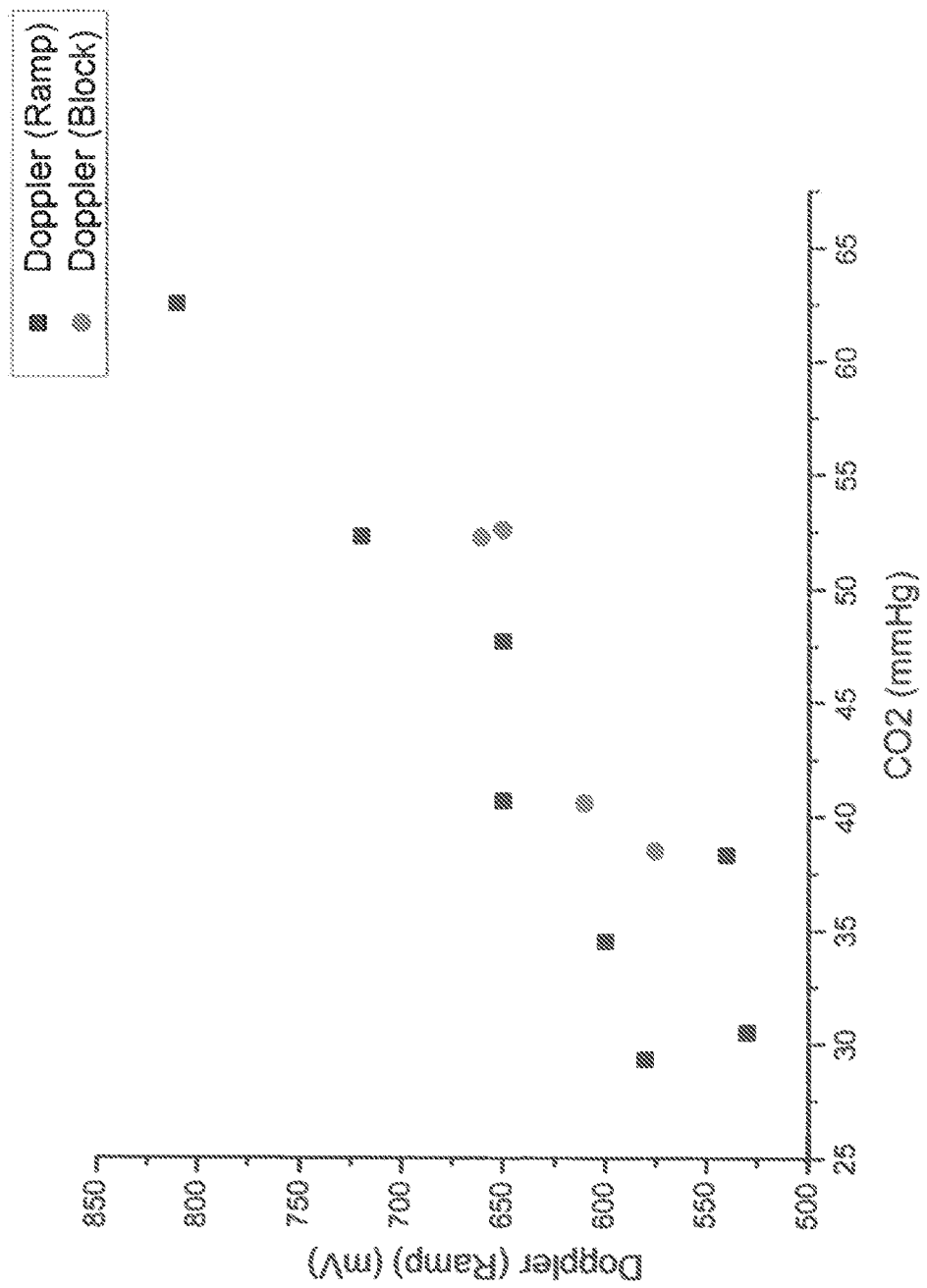
FIG. 5 depicts the Doppler flow through the left anterior descending artery in response to $PaCO_2$ modulation while $PaO_2$ is held constant.

Doppler flow, an ultrasound-based approach which uses sound waves to measure blood flow, was used to show that administration of $CO_2$ leads to vasodilation which results in greater blood flow, while $PaO_2$ is held constant. The Doppler flow was measured in the left anterior descending (LAD) artery. As shown in FIG. 5, as the amount of administered $CO_2$ increases the Doppler flow increases. The relative change in coronary flow velocity is directly proportional to the amount of $CO_2$ administered.

Example 4

Figure 6:
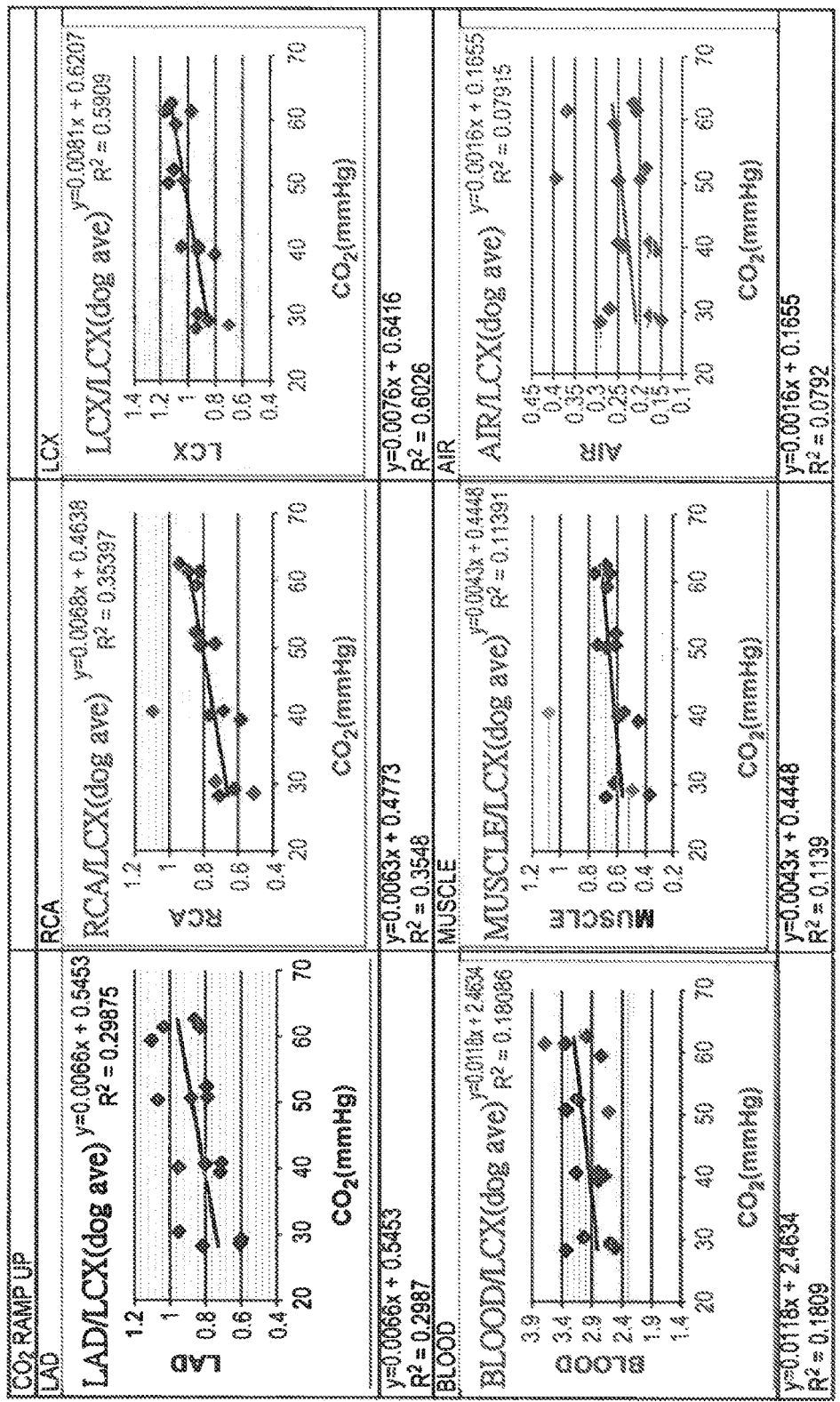
FIG. 6 depicts the Doppler flow through the LAD, RCA and LCX arteries in response to $PaCO_2$ modulation while $PaO_2$ is held constant.
Figure 7:
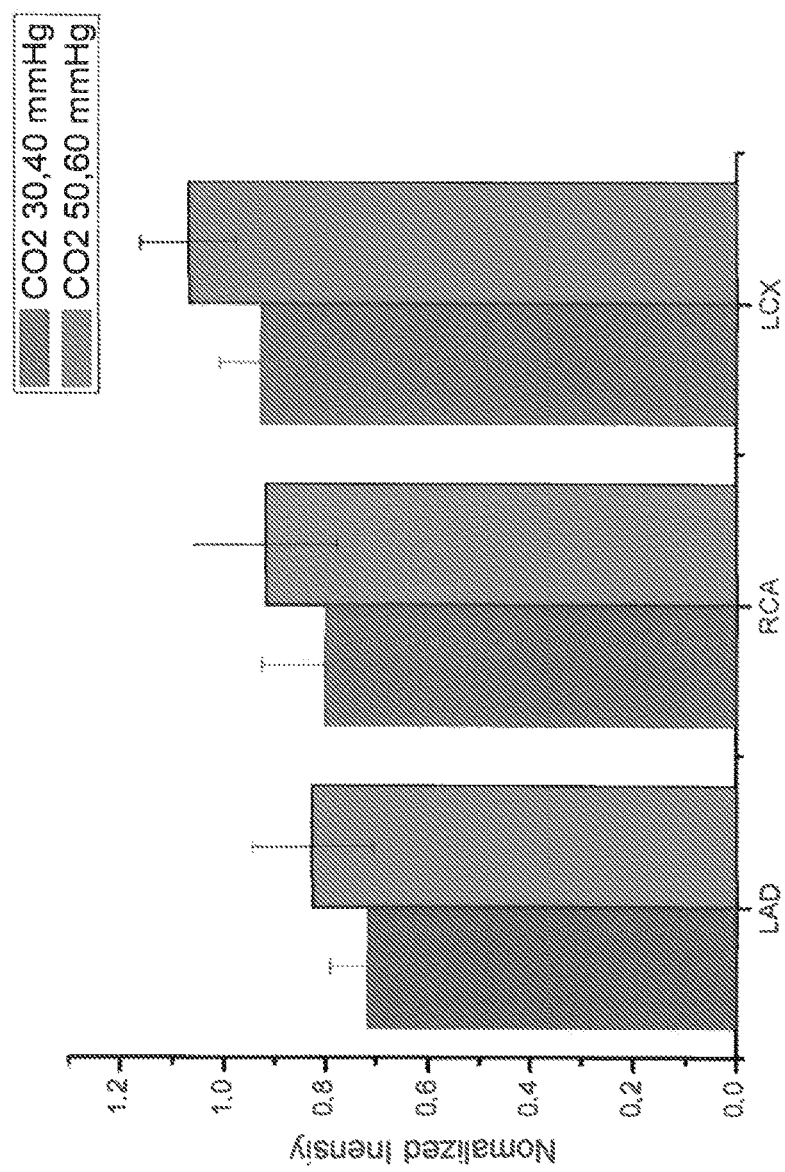
FIG. 7 is a bar graph depicting the territorial myocardial BOLD response to $PaCO_2$ modulations in canines while $PaO_2$ is held constant.
Figure 8:
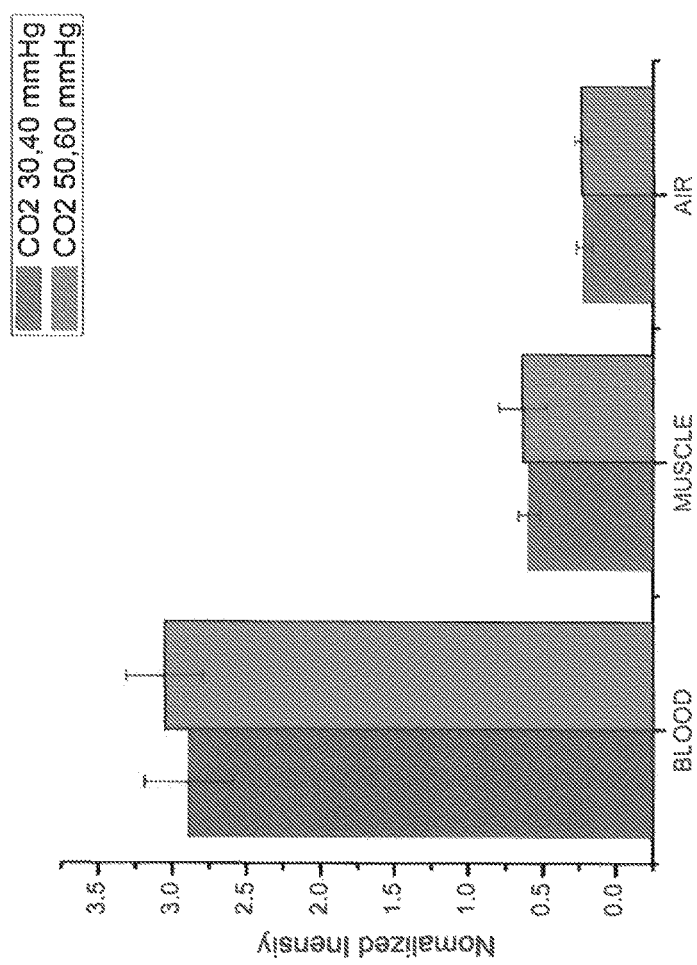
FIG. 8 is a bar graph depicting the BOLD effect associated with $PaCO_2$ modulation in blood, muscle and air while $PaO_2$ is held constant.

Each of the Arteries which Supply Blood to the Myocardium Responds to the $CO_2$ Levels The myocardium is supplied with blood by the left anterior descending (LAD) artery, the right coronary artery (RCA) and the left circumflex (LCX) artery. Applicants measured the blood flow through each of these arteries in response to increasing CO2 supply. As shown in FIG. 6 and summarized in FIG. 7, in each of the three LAD, RCA and LCX arteries, there is a direct correlation between the amount of $CO_2$ administered and the signal intensity; as the amount of administered $CO_2$ increases, the signal intensity, signaling the blood flow, in each of the three arteries increases. Further, as shown in FIG. 6 and summarized in FIG. 8, there is no response to $CO_2$ modulation in control territories such as blood, skeletal muscle or air. As shown in FIG. 9, the mean hyperemic response is approximately 16%.

Example 5

Vascular Reactivity to $CO_2$ Comparable to Adenosine

Figure 10:
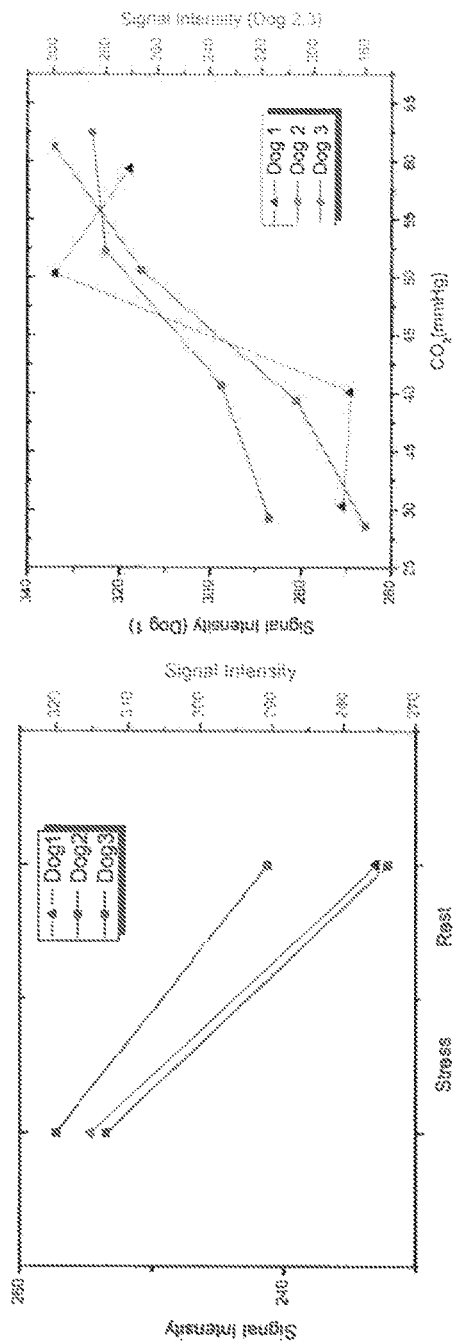
FIG. 10 is a comparison of BOLD response to adenosine and $PaCO_2$ (while $PaO_2$ is held constant).

Vascular reactivity of three canines that were administered with adenosine was compared with the vascular reactivity of canines that were administered with $CO_2$. As shown in FIG. 10, the hyperemic adenosine stress BOLD response is approximately 12% compared with 16% in response to $CO_2$.

Further, as shown in FIG. 11, early human data shows a hyperemic response of approximately 11% for a partial pressure CO2 (pCO2) change of 10 mmHg, from 35 mmHg to 45 mmHg.

Example 6

Figure 12A:
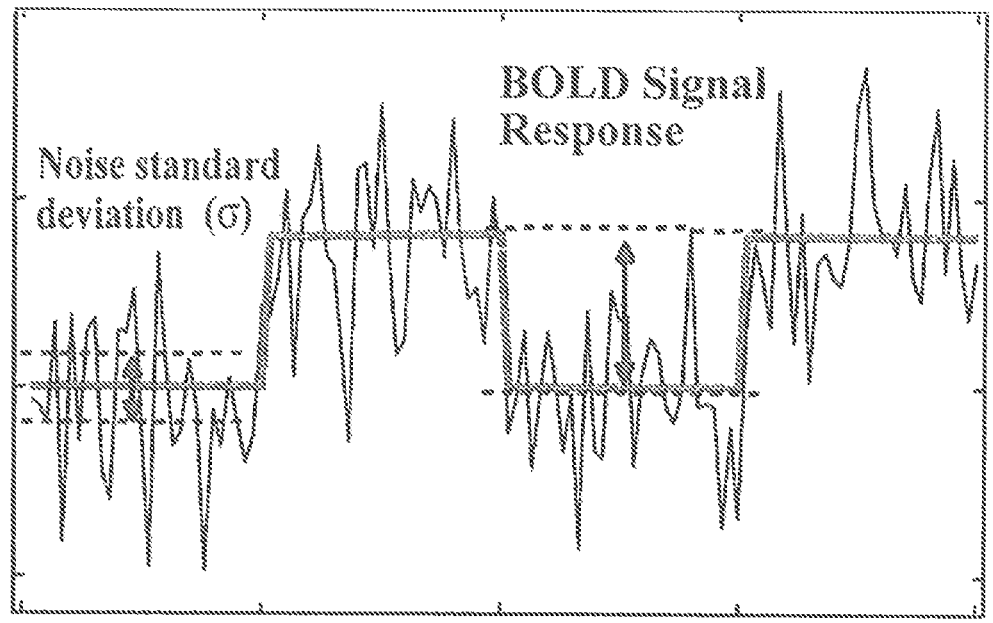
FIG. 12A depicts a simulated BOLD signal for a change in $PaCO_2$ with definitions for noise variability ($\sigma=20$) and response.
Figure 12B:
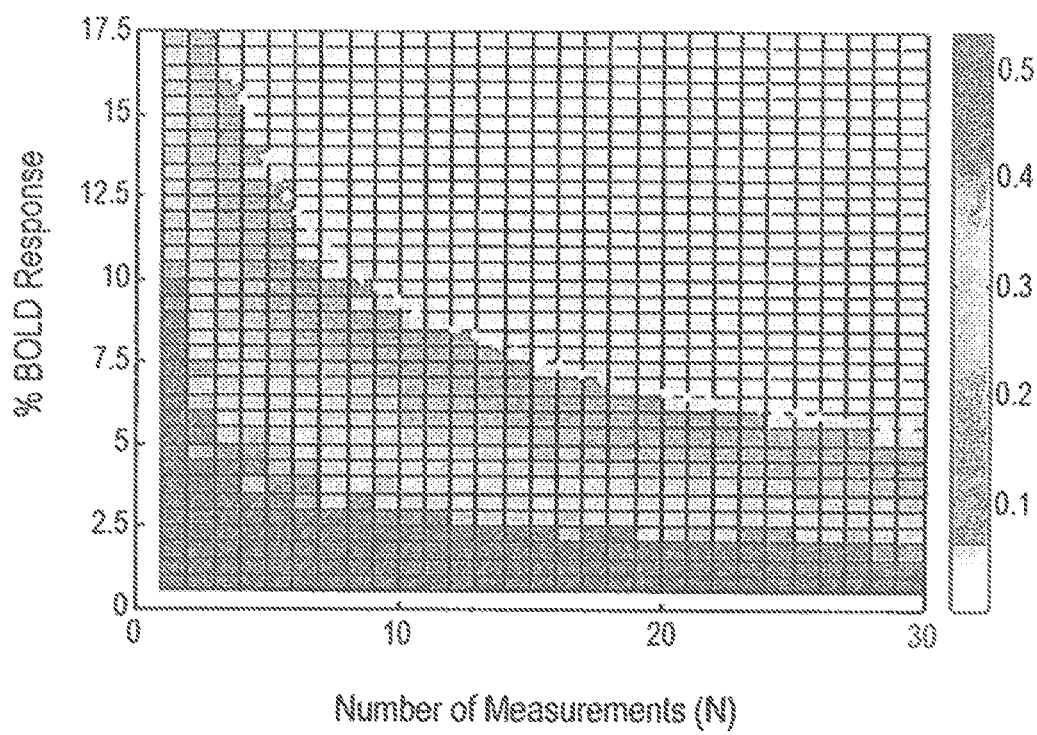
FIG. 12B depicts a relation between BOLD response (y-axis) and the number of measurements (x-axis) required to establish statistical significance (color-coded p-values). For a given BOLD response, the number of repeated measurements (N) required for reliable assessment ($p<0.05$) of a change from baseline condition lies at the right of the white dotted line. For e.g., to reliably detect a BOLD response from a voxel with peak BOLD signal response of 10%, greater than 8 measurements are needed. The bar on the right gives the scale for p values associated with the statistical significance.

To derive a theoretical understanding of how repeated measurements may affect the BOLD signal response, for a given BOLD response to $PaCO_2$, Applicants performed numerical simulations of statistical fits assuming various peak hyperemic BOLD responses to two different $PaCO_2$ levels (as in FIG. 12A) along with known variability in BOLD signals. The results (FIG. 12B) showed that as the BOLD response decreases, the number of measurements required to establish statistical significance ($p<0.05$) associated with the BOLD response increases exponentially. This model provides the basis for developing a statistical framework for identifying ischemic volume on the basis of repeated measures.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of producing coronary vasodilation and monitoring vascular reactivity in a subject comprising:
   (a) administering an admixture comprising carbon dioxide ($CO_2$) to attain two or more predetermined arterial partial pressure of carbon dioxide ($PaCO_2$) levels within a range from 20 mmHg to 65 mmHg in the subject,
      wherein at least two of the two or more predetermined $PaCO_2$ levels exhibit an increase of at least 20 mmHg within the range from 20 mmHg to 65 mmHg and correspond to an increase in $CO_2$ concentration in the administered admixture and/or an increase in length of time of the administered admixture, such that a hyperemic response in the subject's myocardium is induced due to the increase in the $PaCO_2$ level, and
      wherein the admixture is administered for at least one minute to maintain each of the at least two of the two or more predetermined $PaCO_2$ levels;
   (b) imaging the subject's myocardium at each respective maintained level of the at least two of the two or more predetermined $PaCO_2$ levels to obtain respective images corresponding to the increase in the $PaCO_2$ level; and
   (c) quantifying vascular reactivity from the respective images, wherein images obtained at the predetermined $PaCO_2$ level corresponding to the hyperemic response identify a region of the myocardium in which the vascular reactivity is impaired in individuals with coronary heart disease.

2. The method of claim 1, comprising the step of administering a radiotracer to the subject, and wherein the vascular reactivity corresponding to the two or more predetermined $PaCO_2$ levels is monitored using at least one of positron emission tomography (PET) and single photon emission computed tomography (SPECT).

3. The method of claim 1, comprising the step of administering a contrast agent to the subject, and wherein the vascular reactivity corresponding to the two or more predetermined $PaCO_2$ levels is monitored using first-pass perfusion magnetic resonance imaging (MRI).

4. The method of claim 1, wherein the vascular reactivity corresponding to the at least one two or more predetermined $PaCO_2$ levels is monitored using one of blood oxygen-level-dependent (BOLD) MRI and first-pass perfusion MRI.

5. The method of claim 1, wherein the vascular reactivity corresponding to the two or more predetermined $PaCO_2$ levels is monitored via BOLD MRI.

6. The method of claim 1, wherein the admixture comprising $CO_2$ is administered via inhalation.

7. The method of claim 1, wherein the admixture comprising $CO_2$ is administered in a stepwise manner.

8. The method of claim 1, wherein the admixture comprising $CO_2$ is administered to alter the subject's $PaCO_2$ level in a block manner.

9. The method of claim 8, wherein the administering of $CO_2$ to alter the subject's $PaCO_2$ level in a block manner is repeated over time.

10. The method of claim 9, wherein the at least two of the two or more predetermined $PaCO_2$ levels are attained via inhalation of the admixture and are selected from the group consisting of 20 mmHg and 40 mmHg, 20 mmHg and 50 mmHg, 30 mmHg and 50 mmHg, 20 mmHg and 60 mmHg, 30 mmHg and 60 mmHg, and 40 mmHg and 60 mmHg.

11. The method of claim 1, wherein the at least two of the two or more predetermined $PaCO_2$ levels are levels selected from the group consisting of 20 mmHg and 40 mmHg, 20 mmHg and 50 mmHg, 30 mmHg and 50 mmHg, 20 mmHg and 60 mmHg, 30 mmHg and 60 mmHg, 40 mmHg and 60 mmHg, and, 45 mmHg and 65 mmHg.

12. The method of claim 1, wherein the vascular reactivity is monitored using any one or more of positron emission tomography (PET), single photon emission computed tomography (SPECT), computed tomography (CT), magnetic resonance imaging (MRI), single photon emission computed tomography/computed tomography (SPECT/CT), positron emission tomography/computed tomography (PET/CT), ultrasound, electrocardiogram (ECG), Electron-beam computed tomography (EBCT), echocardiogram (ECHO), and electron spin resonance (ESR).

13. The method of claim 1, wherein the subject is selected from the group consisting of a human, a monkey, an ape, a dog, a cat, a cow, a horse, a goat, a pig, a rabbit, a mouse and a rat.

14. The method of claim 1, wherein the administering of the admixture comprising $CO_2$ alters the $PaCO_2$ level in the subject and a $PaO_2$ level in the subject.

15. The method of claim 1, wherein the vascular reactivity is monitored using fractional flow reserve.

16. The method of claim 1, wherein each of the two or more of predetermined $PaCO_2$ levels is a level in a range of 30 to 65 mmHg.

17. The method of claim 16, wherein the admixture maintains each of the at least two of the two or more of predetermined $PaCO_2$ levels for a period of time, the admixture administered for each respective period of time, each respective period of time independently selected from the group consisting of 20 minutes, 15 minutes, 10 minutes, 9 minutes, 8 minutes, 7 minutes, 6 minutes, 5 minutes, 4 minutes, 3 minutes, 2 minutes, and 1 minute.

18. The method of claim 1, wherein the admixture maintains each of the two or more predetermined $PaCO_2$ levels for a period of time, the admixture administered for each respective period of time, each respectively period of time independently selected from the group consisting of 20 minutes, 15 minutes, 10 minutes, 9 minutes, 8 minutes, 7 minutes, 6 minutes, 5 minutes, 4 minutes, 3 minutes, and 2 minutes.

19. The method of claim 1, wherein the administering of the admixture comprising $CO_2$ alters the $PaCO_2$ level in the subject, which does not alter arterial partial pressure of $O_2$ ($PaO_2$).

20. The method of claim 1, wherein the subject has coronary artery narrowing or stenosis, and the method identifies the region of the subject's myocardium in which the vascular reactivity is impaired due to the coronary artery narrowing or stenosis.

21. The method of claim 1, wherein the subject is a human, and the admixture comprising $CO_2$ is administered in a free-breathing manner without anesthesia.

* * * * *